US006607548B2

(12) United States Patent
Pohjonen et al.

(10) Patent No.: US 6,607,548 B2
(45) Date of Patent: Aug. 19, 2003

(54) RESORBABLE POLYMER COMPOSITIONS

(75) Inventors: Timo Pohjonen, Tampere (FI); Harri Happonen, Tampere (FI); Pertti Helevirta, Tampere (FI); Auvo Kaikkonen, Tampere (FI); Jan Nieuwenhuis, Gorinchem (NL); Piet E. Haers, Surrey (GB); Hermann Sailer, Zurich (CH)

(73) Assignee: Inion Ltd., Tampere (FI)

( * ) Notice: Subject to any disclaimer, the term of this patent is extended or adjusted under 35 U.S.C. 154(b) by 0 days.

(21) Appl. No.: 09/859,734

(22) Filed: May 17, 2001

(65) Prior Publication Data

US 2002/0173595 A1 Nov. 21, 2002

(51) Int. Cl.⁷ ................................................ A61B 17/56
(52) U.S. Cl. ........................ 606/230; 606/60; 606/69; 606/77; 606/86; 606/105; 606/231
(58) Field of Search ................................ 606/230, 231, 606/60, 69, 77, 86, 105

(56) References Cited

U.S. PATENT DOCUMENTS

| | | | |
|---|---|---|---|
| 4,905,680 A | 3/1990 | Tunc | 606/69 |
| 5,314,989 A | 5/1994 | Kennedy et al. | 528/354 |
| 5,372,598 A | 12/1994 | Luhr et al. | 606/69 |
| 5,403,347 A | 4/1995 | Roby et al. | 606/230 |
| 5,468,242 A | 11/1995 | Reisberg | 606/69 |
| 5,502,159 A | 3/1996 | Liu et al. | 528/354 |
| 5,569,250 A | 10/1996 | Sarver et al. | 606/69 |
| 5,690,631 A | 11/1997 | Duncan et al. | 606/69 |
| 5,700,901 A | 12/1997 | Hurst et al. | 528/354 |
| 5,868,746 A | 2/1999 | Sarver et al. | 606/69 |
| 6,093,201 A | 7/2000 | Cooper et al. | 606/232 |
| 6,130,271 A | 10/2000 | Jarrett et al. | 523/113 |

FOREIGN PATENT DOCUMENTS

| | | |
|---|---|---|
| EP | 0 199 074 A1 | 10/1986 |
| WO | WO 94/11441 | 5/1994 |

*Primary Examiner*—Ana Woodward
(74) *Attorney, Agent, or Firm*—Banner & Witcoff, Ltd.

(57) ABSTRACT

A novel polymer composition is provided which includes a base material including a biodegradable polymer or copolymer, and a copolymer additive including one or more monomers imparting a tensile strength to the polymer composition at room temperature that is lower than a tensile strength at room temperature for the base material.

12 Claims, 11 Drawing Sheets

Research matrix: R1LF
Product: 2.0 x 38 mm 6-hole scalloped plate
Manufacturing method: Injection molding Material:

| | A | B | C | D | E | F |
|---|---|---|---|---|---|---|
| Composition | PLLA/TMC 70:30 | P(L/DL)LA 70:30 | P(L/DL)LA 70:30 | P(L/DL)LA 80:20 | PLGA 85:15 | PLGA 80:20 |

Materialcombinations:

| Recipe number | Material A (w.-%) | Material B (w.-%) | Material C (w.-%) | Material D (w.-%) | Material E (w.-%) | Material F (w.-%) |
|---|---|---|---|---|---|---|
| R1LF-1 | 0 | 100 | | | | |
| R1LF-2 | 20 | 80 | | | | |
| R1LF-3 | 30 | 70 | | | | |
| R1LF-4 | 40 | 60 | | | | |
| R1LF-5 | 50 | 50 | | | | |
| R1LF-6 | 100 | 0 | | | | |
| R1LF-7 | 0 | | 100 | | | |
| R1LF-8 | 20 | | 80 | | | |
| R1LF-9 | 30 | | 70 | | | |
| R1LF-10 | 40 | | 60 | | | |
| R1LF-11 (not to be made) | 50 | | 50 | | | |
| R1LF-12 | 0 | | | 100 | | |
| R1LF-13 | 20 | | | 80 | | |
| R1LF-14 | 30 | | | 70 | | |
| R1LF-15 | 40 | | | 60 | | |
| R1LF-16 | 50 | | | 50 | | |
| R1LF-17 | 0 | | | | 100 | |
| R1LF-18 | 20 | | | | 80 | |
| R1LF-19 | 30 | | | | 70 | |
| R1LF-20 | 40 | | | | 60 | |
| R1LF-21 (not to be made) | 50 | | | | 50 | |
| R1LF-22 | 0 | | | | | 100 |
| R1LF-23 | 20 | | | | | 80 |
| R1LF-24 | 30 | | | | | 70 |
| R1LF-25 | 40 | | | | | 60 |
| R1LF-26 (not to be made) | 50 | | | | | 50 |

RESORBABLE POLYMER COMPOSITIONS

BACKGROUND OF THE INVENTION

1. Field of the Invention

Embodiments of the present invention relate generally to novel polymer compositions which are useful in the manufacture of medical implants. More particularly, embodiments of the present invention relate to blended polymer compositions having an additive ingredient, which produces a blend having a lower tensile strength when compared to the polymer composition without the additive ingredient. The blended polymer compositions are biodegradable or bioresorbable. Methods of lowering the tensile strength of a copolymer are also disclosed. The novel polymer compositions can be fashioned into medical implants for implantation in the body.

2. Description of Related Art

Biodegradable polymer materials and blends thereof used for the production of implants, and implants themselves, are known. See for example U.S. Pat. Nos. 5,700,901; 5,502,159; 5,868,746; 5,569,250; 6,093,201; 5,314,989; 5,403,347; 5,372,598; 4,905,680; 5,468,242; and 5,690,631 each of which are hereby incorporated by reference in their entireties for all purposes. However, blends of polymers with copolymers which result in reduced tensile strength of the implant fashioned therefrom and resulting cold-bendable properties have not been disclosed.

SUMMARY OF THE INVENTION

Embodiments of the present invention relate generally to novel polymer compositions which are useful in the manufacture of medical implants. The polymer compositions are biocompatible and bioresorbable. According to one embodiment of the present invention, a lactic acid or glycolic acid based polymer or copolymer is blended with one or more copolymer additives. The resulting blend is used to form an implant, for example, by well known methods such as melt blending and injection molding and the like. The resulting implant exhibits a lower tensile strength and a higher ductility when compared to an implant formed from a polymer or copolymer lacking the one or more copolymer additives. A copolymer additive according to the present invention includes a bioresorbable monomer and a monomer capable of lowering the tensile strength of the overall polymer composition. As a result, implants fashioned from the novel polymer compositions of the present invention exhibit advantageous properties of being cold-bendable, i.e. bendable at room temperature without crazing or cracking. In addition, the implants of the present invention are capable of being rejuvenated, i.e. cold-bendable properties which may be reduced over long periods of time can be restored by warming the implant.

Embodiments of the present invention also include methods of making implants and the resulting implants themselves which exhibit reduced tensile strength due to the incorporation of the copolymer additive into a bioresorbable polymer or copolymer either before or during the extrusion process. According to the method, a bioresorbable polymer or copolymer is provided. The bioresorbable polymer or copolymer can be mixed with the copolymer additive and then the mixture melt-blended. Alternatively, the individual components can be melted separately or sequentially and then blended together prior to an injection molding process.

Embodiments of the present invention are still further directed to methods of recovering initial physical properties of implants formed from the polymer compositions of the present invention. According to the present invention, physical properties of implants formed from the present invention are allowed to change through, for example, the passage of time as can be associated with shelf life. The implant is then heated, for example, on a temperature controlled heating plate for a time period sufficient to restore approximately the initial physical properties of the implant.

Accordingly, it is an object of the present invention to provide polymer compositions having reduced tensile strength and increased ductility. It is another object of the present invention to provide polymer compositions useful in the production of biodegradable or bioresorbable implants. It is yet another object of the present invention to provide a method of altering the tensile strength of implants to accommodate a particular implant use. It is still yet another object of the present invention to provide a biodegradable or bioresorbable implant which is cold bendable, i.e. bendable at room temperature without crazing or cracking. It is a further object of the invention to eliminate the need for the preheating of implants prior to implantation into the body. It is a yet further object of the present invention to provide a method of restoring approximately the initial physical properties of the implant. These and other objects, features and advantages of the present invention will become apparent from the following description taken in conjunction with the accompanying drawings.

DETAILED DESCRIPTION OF CERTAIN PREFERRED EMBODIMENTS

The principles of the present invention may be applied with particular advantage to provide novel implants formed from polymer compositions that exhibit advantageous tensile properties. In a particular aspect, a melt-blended polymer composition is provided that includes a base material including a biodegradable polymer or copolymer, and a copolymer additive including one or more monomers imparting, providing or otherwise altering a tensile strength to or of the melt-blended polymer composition at room temperature that is lower than a tensile strength at room temperature for the base material. The polymer compositions of the present invention can be used to form implants having desirable properties by processing steps including injection molding, extrusion, pressure melting, hot pressing and other like methods known to those skilled in the art. The terms "injection molding" and "injection molded" should in no way be interpreted as the only means for producing the implants of the present invention. One aspect of the invention, rather, relates to implants which have been produced or modified by thermoplastic deformation.

According to the present invention, a biodegradable polymer or copolymer is provided as an initial base material and is then combined with one or more copolymer additives to alter the tensile properties of the biodegradable polymer or copolymer. According to one embodiment of the present invention, the biodegradable polymer or copolymer, i.e. base material, is a polymer or copolymer of lactic acid, L-lactide, D-lactide, D,L-lactide, meso-lactide, glycolic acid, glycolide and the like and optionally other cyclic esters which are copolymerizable with lactide. Additional co-monomers may also be present to impart desired properties as needed such as alpha-, beta- or gamma-hydroxybutyric acid, alpha-, beta- or gamma-hydroxyvaleric acid and other hydroxy fatty acids ($C_{11}$ to $C_{25}$) such as stearic acid, palmitic acid, oleic acid, lauric acid and the like. Accordingly, base material of the present invention include polylactides, polyglycolides, poly(L-lactide), poly (D-lactide), poly(L-lactide-co-D,L-lactide), poly(L-lactide-co-meso-lactide), poly(L-lactide-co-glycolide), poly(L-lactide-co-epsilon-caprolactone), poly(D,L-lactide-co-meso-lactide), poly(D,L-lactide-co-glycolide), poly(D,L-lactide-co-epsilon-caprolactone), poly(meso-lactide-co-glycolide), poly(meso-lactide-co-epsilon-caprolactone) and the like. When the base material is a copolymer, the monomer units are present in a ratio of 50:50, 60:40, 70:30, 80:20, 85:15 and all suitable ratios in between. For example, suitable base materials include poly(L-lactide-co-D,L-lactide) 70:30, poly(L-lactide-co-D,L-lactide) 80:20, poly(L-lactide-co-glycolide) 85:15, and poly(L-lactide-co-glycolide) 80:20. Copolymers that contain L-lactide as a component preferably contain at least 70% of the L-lactide component and more preferably between about 70% and about 95% of the L-lactide component. Polymers or copolymers useful as base materials are commercially available from many sources or can be readily manufactured using methods well-known to those skilled in the art.

In accordance with the present invention, the copolymer additive of the present invention is based on a biodegradable monomer and a monomer that alters the tensile property of the resulting implant. The monomers that are included into the copolymer additive can be in any sequence. For example, the copolymer additive includes both random copolymers and block copolymers. According to one embodiment of the present invention, the copolymer additives are those including one or more of lactic acid, L-lactide, D-lactide, D,L-lactide, meso-lactide, glycolic acid, glycolide and the like along with one or more of trimethylene carbonate and dioxanone. Certain advantageous copolymer additives within the scope of the present invention include poly(L-lactide-co-trimethylene carbonate), poly(D,L-lactide-co-trimethylene carbonate), poly(meso-lactide-co-trimethylene carbonate), poly(glycolide-co-trimethylene carbonate), poly(L-lactide-co-dioxanone), poly(D,L-lactide-co-dioxanone), poly(meso-lactide-co-dioxanone), and poly(glycolide-co-dioxanone) and the like. Polymers or copolymers useful as base materials are commercially available from many sources or can be readily manufactured using methods well-known to those skilled in the art.

According to the present invention, incorporation of copolymer additives including trimethylene carbonate and/or dioxanone to the base materials results in implants and other devices fashioned therefrom having an increased elongation at break and also a lowered tensile strength. It is particularly advantageous in the implants of the present invention to exhibit lowered tensile strength as the resulting implants are cold bendable, i.e. bendable at room temperature without visual confirmation of crazing or cracking. The advantageous cold-bendable implants of the present invention allow the user greater mobility in contouring the implants to uneven or curved surfaces without unduly stressing the implant itself. Accordingly, it is a particularly useful aspect of the present invention to lower the tensile strength of implants formed from biodegradable polymers or copolymers alone by blending base materials with the polymer additives of the present invention. The resulting cold-bendable implants avoid the use of heating systems to preheat otherwise brittle implants to a ductile state prior to implantation onto a contoured surface in the body.

In accordance with another aspect of the present invention, a method is provided to produce an implant having a resulting crystallinity that is lower than the crystallinities of the individual polymers or copolymers which are blended together to produce the implant. Accordingly, a base polymer or copolymer having a certain crystallinity is blended with a copolymer additive having a certain crystallinity. The resulting blend which may be in the form of an implant has a crystallinity that is lower than the crystallinity of either the base polymer or the copolymer additive. The lower crystallinity results in the blend having a lower tensile strength as compared to the base polymer alone. In accordance with this aspect of the invention, a blend is produced wherein the blend is characterized as being in a continuous phase or alternatively in a discontinuous phase.

In accordance with another aspect of the present invention, a method is provided to produce an implant of a blend of a base polymer or copolymer and an additive copolymer having a resulting glass transition temperature that is lower than the glass transition temperature of the base polymer or copolymer alone. Accordingly, a base polymer or copolymer having a certain glass transition temperature is blended with a copolymer additive. The resulting blend which may be in the form of an implant has a glass transition temperature that is lower than the glass transition temperature of the base polymer or copolymer. The lower glass transition temperature results in the blend having a lower tensile strength as compared to the base polymer alone.

Figure 1:
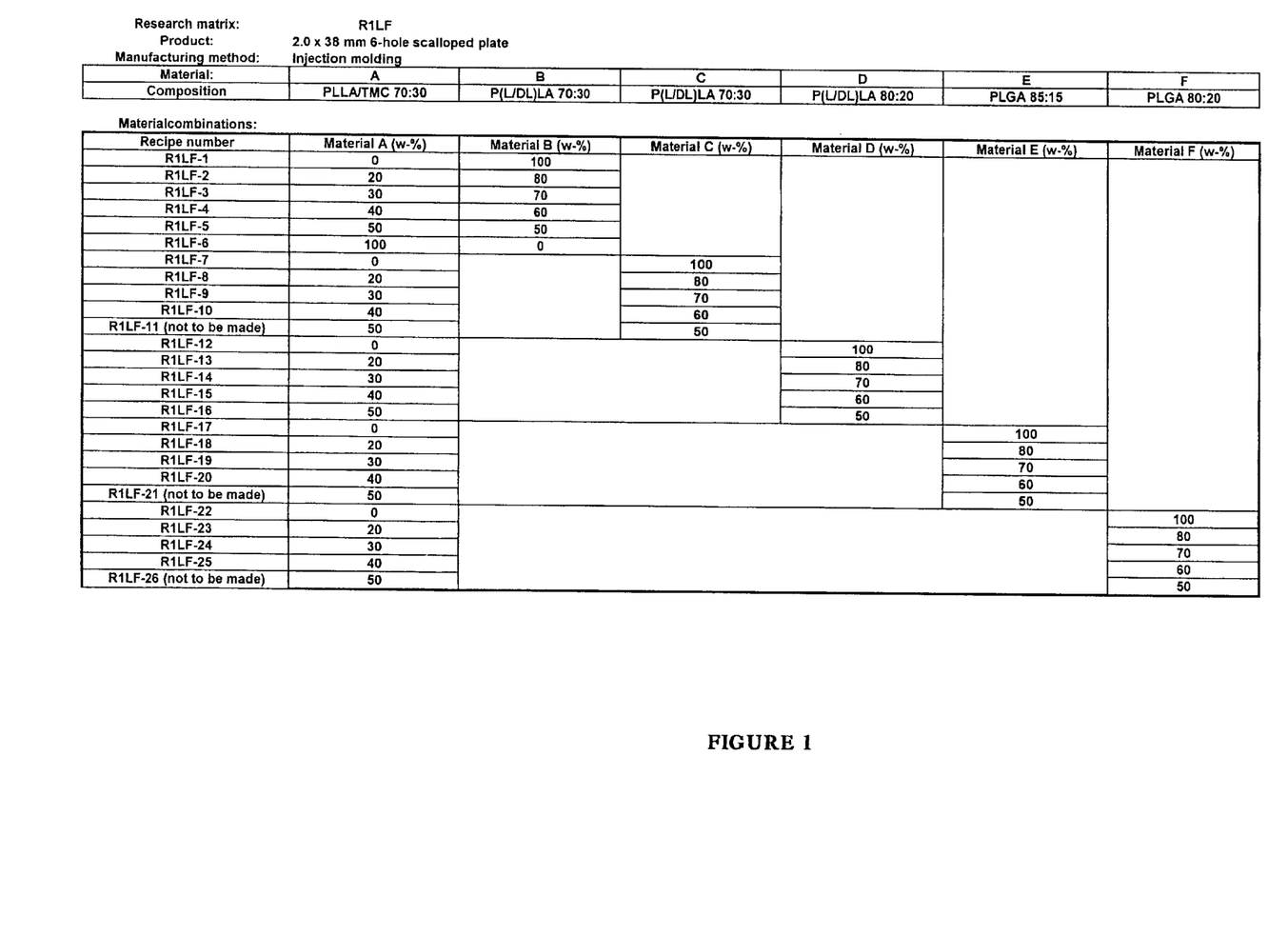
FIG. 1 is a table showing different polymer compositions used to manufacture injection molded plate test pieces.

According to certain aspects of the present invention, the mixtures or blends of the present invention include the base material in an amount between about 50% and about 99%. Likewise, the polymer or copolymer additive is present in an amount between about 1% and about 50% depending upon the initial amount of the base material chosen and the desired reduction in tensile strength. FIG. 1 identifies 25 different compositions that have been formulated and used to create an injection molded plate test piece. The base materials included poly(L-lactide-co-D,L-lactide) 70:30, poly(L- lactide-co-D,L-lactide) 80:20, poly(L-lactide-co-glycolide) 85:15, and poly(L-lactide-co-glycolide) 80:20 in the percentage amounts indicated in FIG. 1. The polymer additive was poly(L-lactide-co-trimethylene carbonate) 70:30 in the percentage amounts indicated in FIG. 1.

The following examples are intended to illustrate certain embodiments of the present invention and are not intended to be limiting in any manner.

EXAMPLE I

Preparation of Polymer Compositions

In general, the polymer compositions identified in FIG. 1 were prepared by manually mixing commercially available base materials with commercially available copolymer additives. The resulting mixture was then melt blended and injection molded into plate test pieces. The plate test pieces were then tested for elongation at break, tensile force at break and tensile strength according to the following protocols.

More specifically, the polymer compositions were prepared by dry mixing commercially available granular materials with commercially available copolymer additives. The components were weighed according to the desired weight ratio into a container which was then rotated in a Turbula T2F shaker mixer for 30 minutes until a homogenous dry mixture was obtained. The resulting mixture was subsequently dried in vacuum at 60° C. for 6 hours and thereafter melt blended and injection molded into plate test pieces. The plate test pieces were then tested for elongation at break, tensile force at break and tensile strength according to the following protocols. The injection-molding machine used was a fully electric Fanuc Roboshot Alpha i30A-injection molding machine with a mould clamping force of 300 kN. The injection unit was equipped with high speed (max. 66 cm³/s–330 mm/s), high pressure (max. 2500 bar) injection options. The barrel diameter was 16 mm and was equipped with three band heater zones, a standard profile anticorrosion screw, and a standard open nozzle with a 2.5 mm hole. The extruder melt blending and homogenization conditions of the material during metering phase of the process included a back pressure of 40–60 bar, a screw speed of 60–100 rpm, and barrel temperatures of 160–230° C. The injection molding conditions included a nozzle temperature of 180–230° C., an injection speed of 80–300 mm/s, a maximum injection pressure of 2500 bar, a pack pressure of 1000–2300 bar for 3 to 8 seconds, a cooling time of 10 to 22 seconds and a mould temperature of 20–30° C.

The total cycle time was 20 to 40 seconds consisting of the following phases during one injection molding process cycle: closing of the mould, injection of the molten polymer into the mould, pack pressure, cooling (extruder metering for the next cycle during cooling phase), opening the mould, and ejection of the plate.

EXAMPLE II

Determining Elongation at Break

According to the following protocol, the elongations at break of various injection molded plates were determined.

A Zwick Z020/TH2A universal materials testing machine with 10 kN load cell was used to determine elongation at break of the test plates. Gamma sterilized plates were tested at room temperature just after opening the sterile package or at 37° C. in water bath after 30 minutes of preconditioning in water at 37° C. Plates were fixed with three pins through the holes of the plate in both ends of the plate. Plates were loaded with the constant speed of 5 mm/min until break of the plate. Elongation at break was determined in millimeters (mm) according the standard (ASTM D638M). Crosshead movement of the universal materials testing machine was used to measure extension of the specimen.

EXAMPLE III

Determining Tensile Force at Break

According to the following protocol, the tensile force at break of various injection molded plates were determined.

A Zwick Z020/TH2A universal materials testing machine with 10 kN load cell was used to determine tensile force at break of the test plates. Gamma sterilized plates were tested at room temperature just after opening the sterile package or at 37° C. in water bath after 30 minutes preconditioning in water at 37° C. Plates were fixed with three pins through the holes of the plate in both ends of the plate. Plates were loaded with the constant speed of 5 mm/min until break of the plate. Tensile force at break was determined in Newtons (N) according the standard (ASTM D638M).

EXAMPLE IV

Determining Tensile Strength

According to the following protocol, the tensile strength of various injection molded plates were determined.

Zwick Z020/TH2A universal materials testing machine with 10 kN load cell was used to determine tensile strength of the test plates. Gamma sterilized plates were tested at room temperature just after opening the sterile package or at 37° C. in water bath after 30 minutes preconditioning in water at 37° C. Plates were fixed with three pins through the holes of the plate in both ends of the plate. Plates were loaded with the constant speed of 5 mm/min until break of the plate. Maximum load was measured in Newtons (N) and tensile strength was determined according the standard (ASTM D638M).

$$\sigma = \frac{F\max}{A\min}$$

Where
$\sigma$=Tensile strength (MPa)
F max=Maximum load (N)
A min=Minimum cross section area of the plate (mm²)

EXAMPLE V

Testing Data

Figure 2:
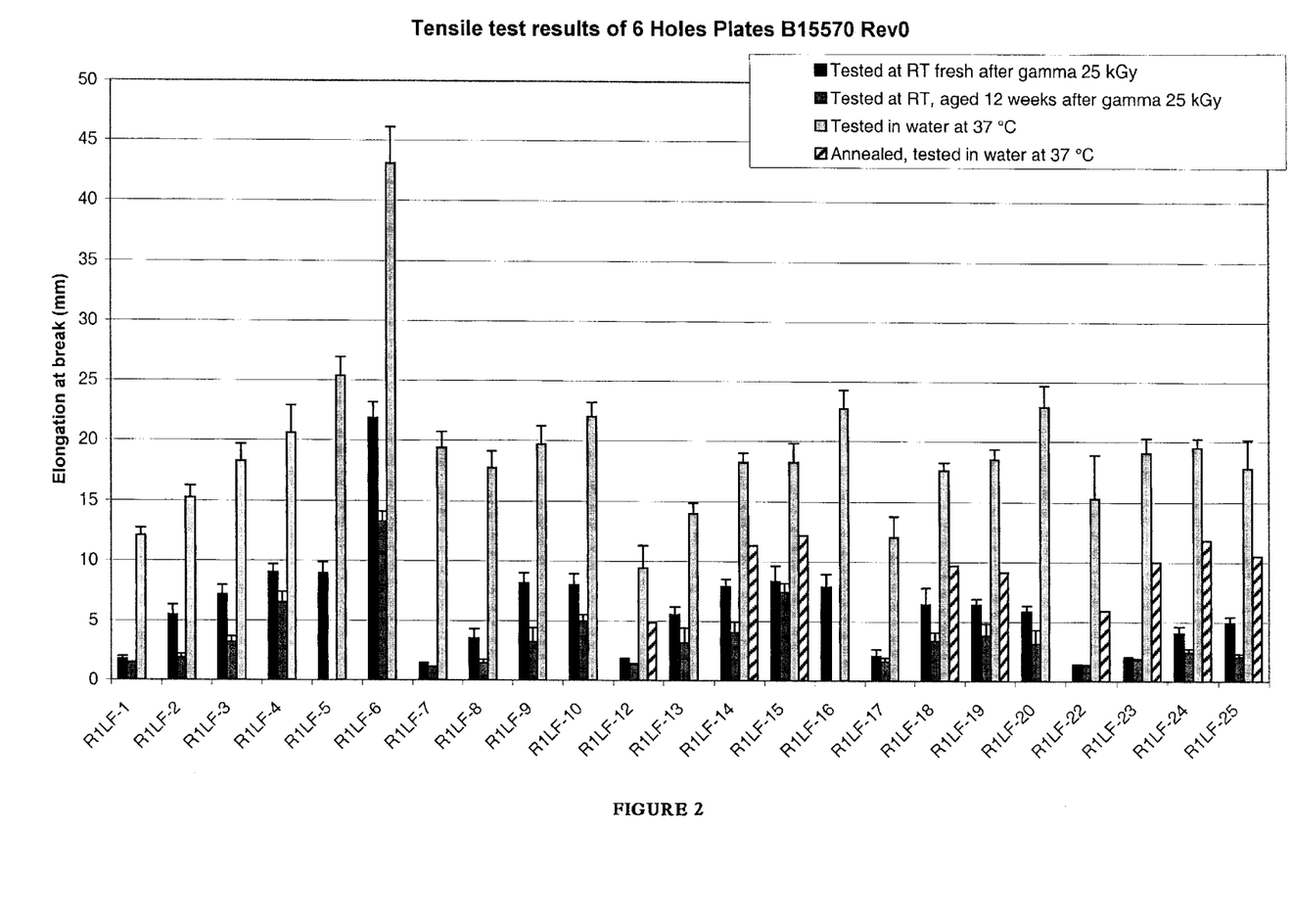
FIG. 2 is graph of the elongation at break of 25 implants produced by different polymer compositions at room temperature and at 37° C.

FIG. 2 is a graph of the elongations at break of various injection molded test plates of FIG. 1 at room temperature (RT) and at 37° C. R1LF-1 is a commercially available polymer composition for use in certain cranial-maxillo-facial plating systems. As can be seen in FIG. 2, the elongation at break at room temperature and at 37° C. generally increases as the amount of copolymer additive increases. The low elongation at break for the commercially available material represented by R1LF-1 which lacks the copolymer additive indicates that the test plate is brittle at room temperature and is not cold-bendable. According to the present invention, a test piece is cold-bendable when the test piece exhibits an elongation at break of greater than 5%.

Figure 3:
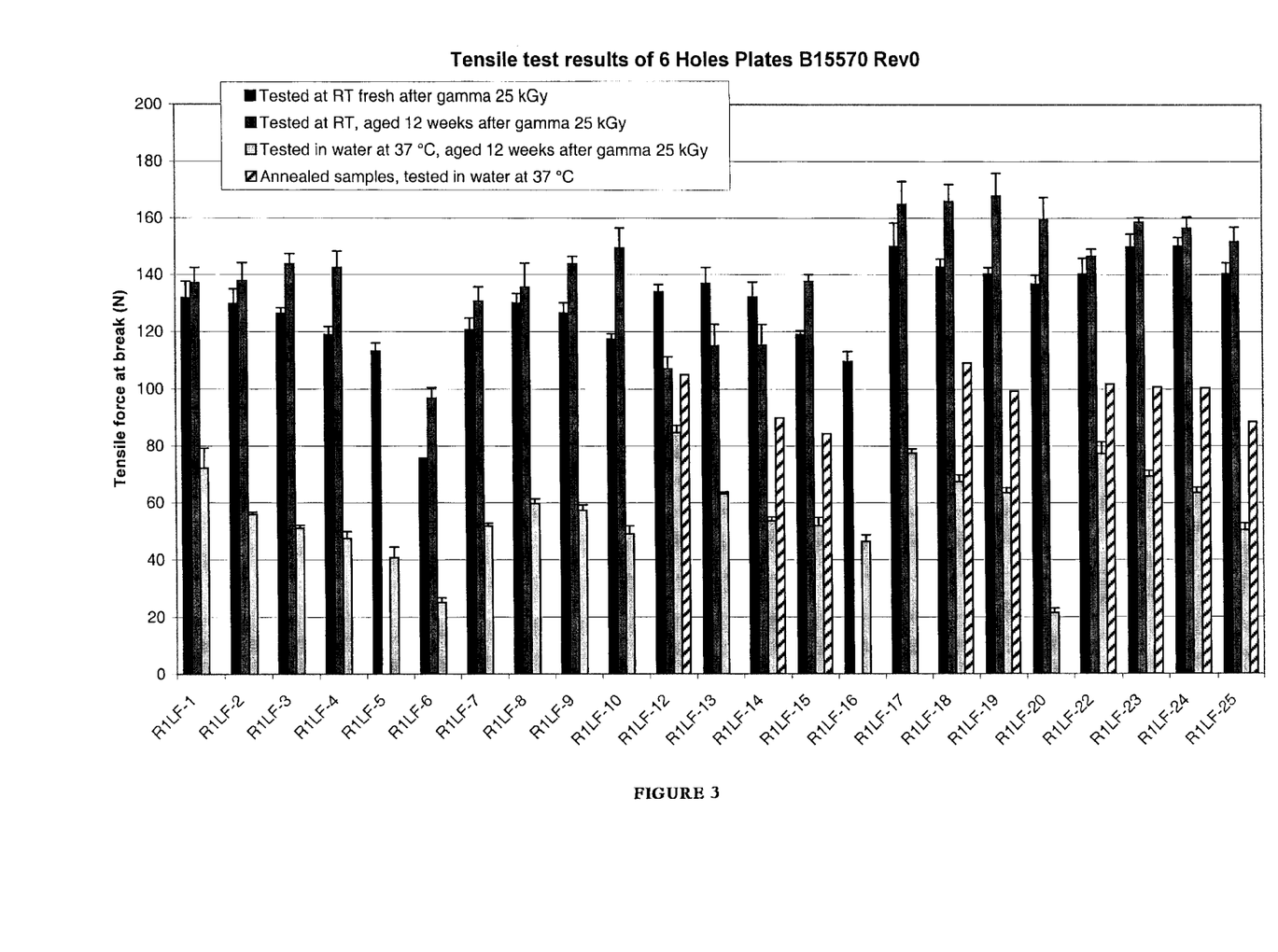
FIG. 3 is a graph of tensile force at break of 25 implants produced by different polymer compositions at room temperature and at 37° C.

FIG. 3 is a graph of tensile force at break for the test plates of FIG. 1. As can be seen in FIG. 3, tensile force at break at room temperature and at 37° C. generally decreases as the amount of copolymer additive increases. In addition, the tensile force at break increases after annealing indicating improved stability of the test plates.

Figure 4:
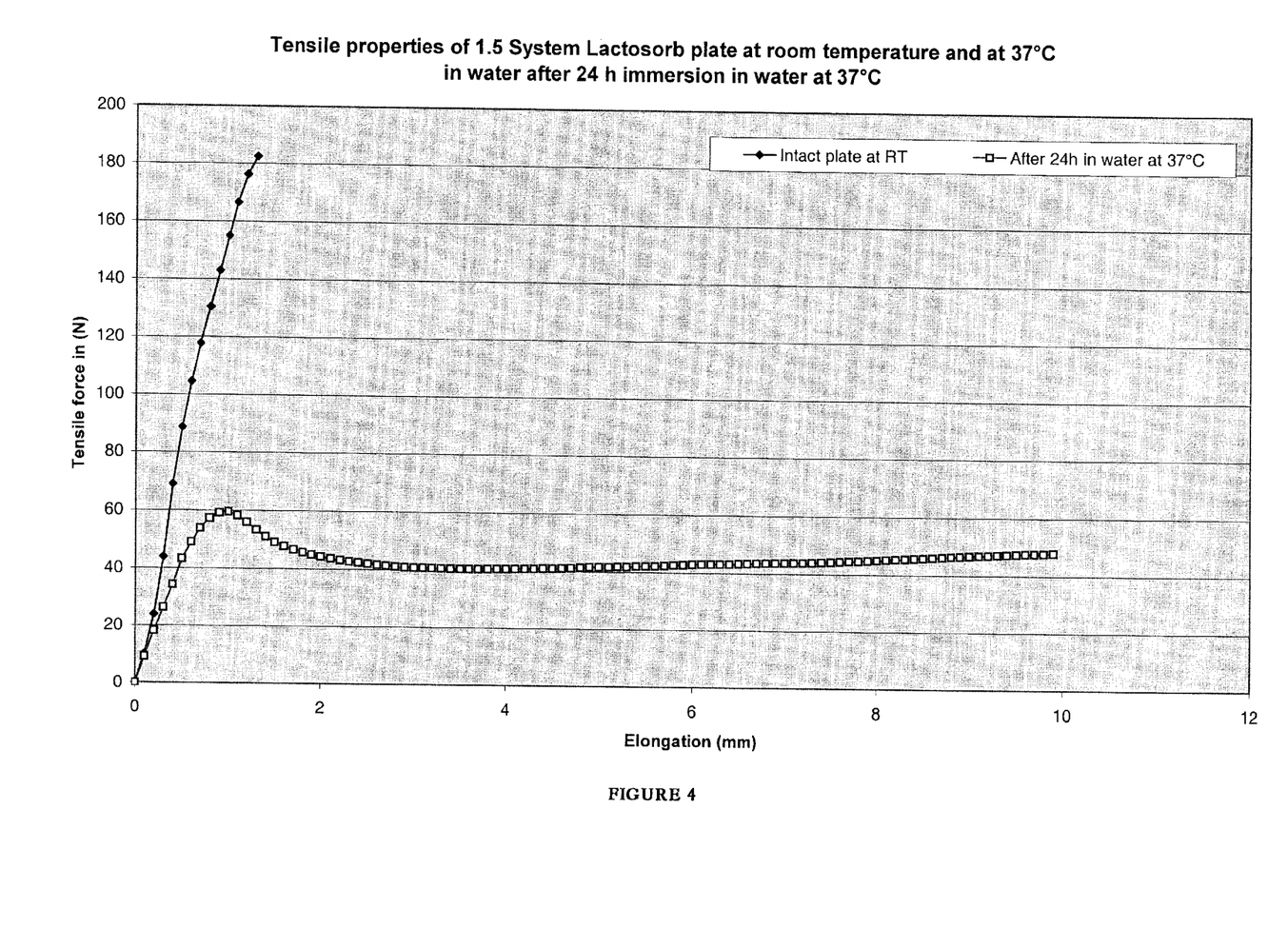
FIG. 4 is a graph of tensile force in newtons of a prior art device known as LACTOSORB.

FIG. 4 is a graph of the tensile force versus elongation for a commercially available plate known under the trade name LACTOSORB formed from a block copolymer of 82% glycolide and 18% L-lactide at room temperature and at 37° C. The data demonstrates that the LACTOSORB plate which lacks a copolymer additive of the present invention is brittle at room temperature and not cold bendable.

Figure 5:
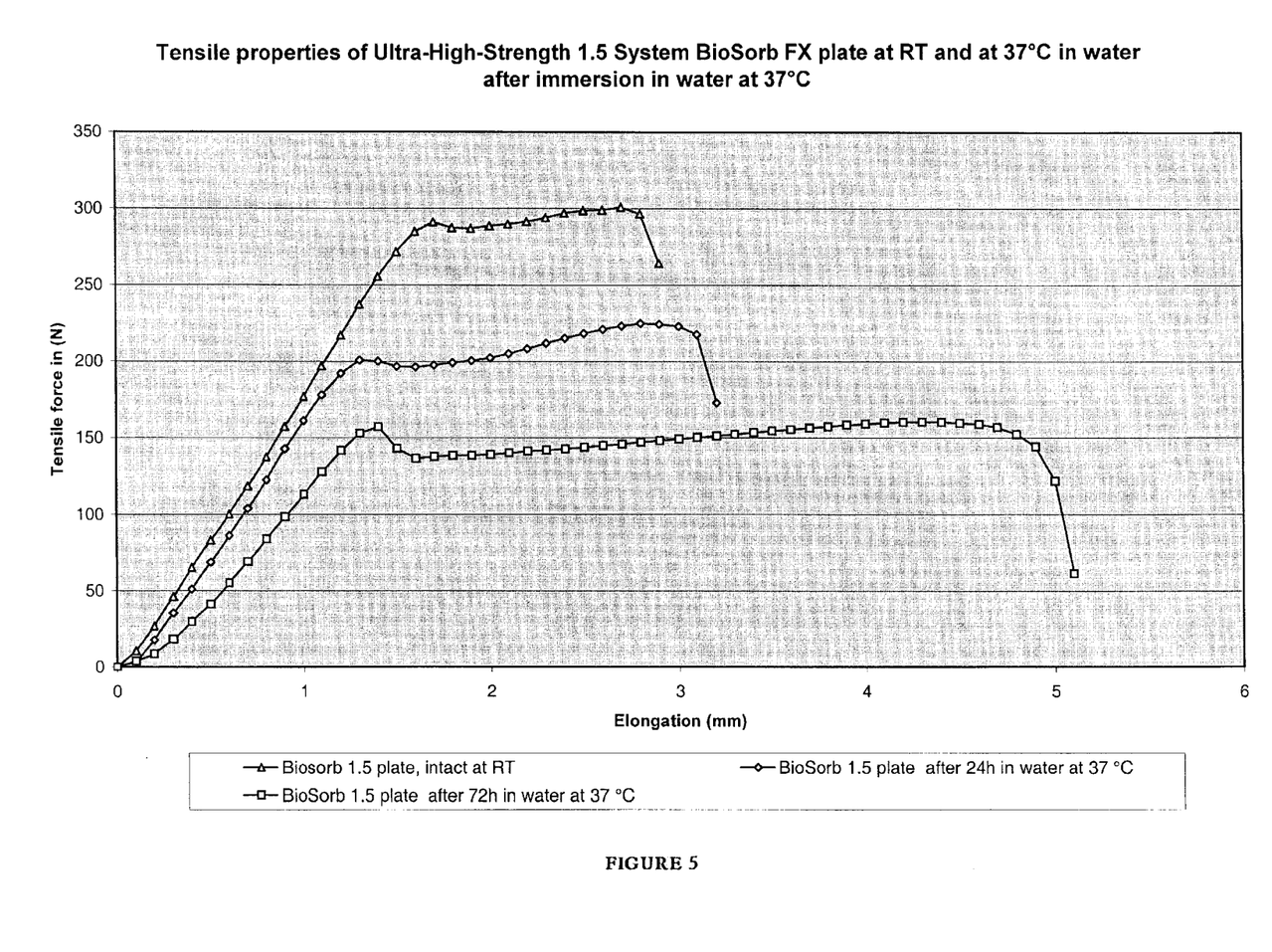
FIG. 5 is a graph of tensile force in newtons of a prior art device known as BIOSORB FX.

FIG. 5 is a graph of the tensile force versus elongation for a commercially available plate known under the trade name BIOSORB formed from reinforced poly(L-lactide-co-glycolide) 70:30 at room temperature and at 37° C. The data demonstrates that the BIOSORB plate is not as brittle as the LACTOSORB plate, however, the BIOSORB plate is self reinforced which detracts from bending strength. Further, the BIOSORB plate cannot be shaped once heated in water and also shrinks in size after heating.

Figure 6:
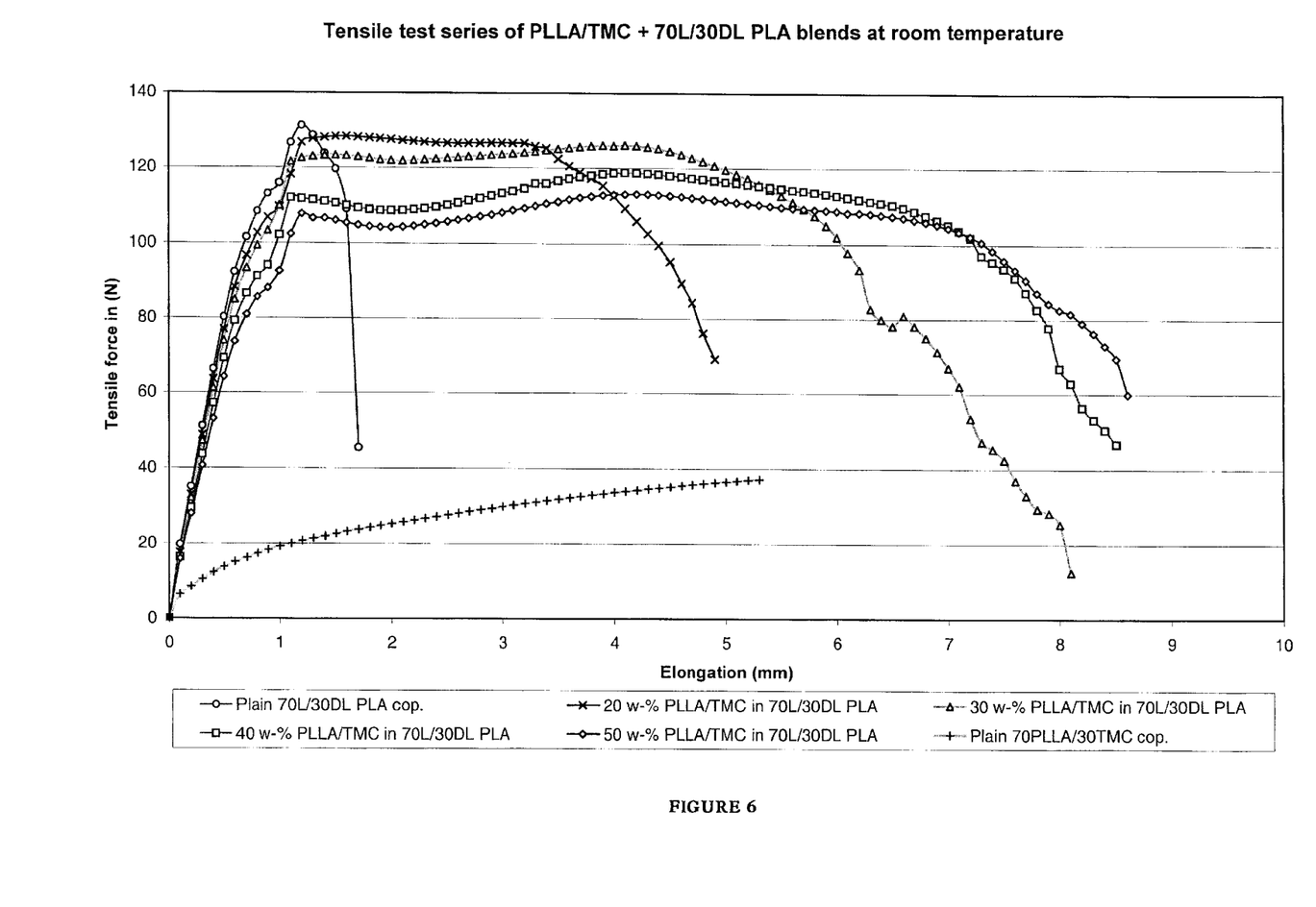
FIG. 6 is a graph of tensile force in newtons versus elongation for various implants at room temperature.

FIG. 6 is a graph of tensile force versus elongation at room temperature for a test plate which excludes a copolymer additive of the present invention and test plates which include copolymer additives of the present invention. The test piece which excludes the copolymer additive has a failure at 1.5 mm strain indicating that the material is not cold bendable.

Figure 7:
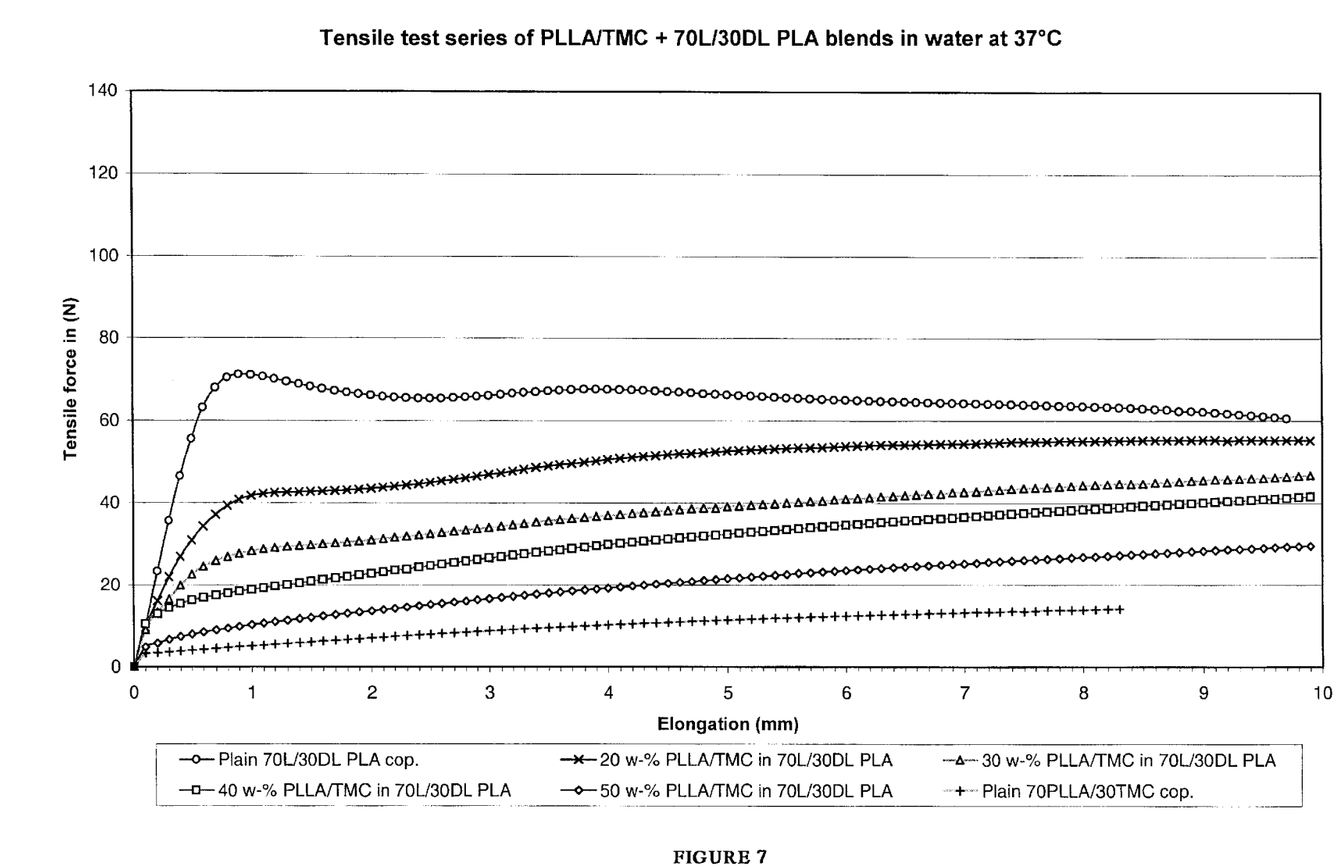
FIG. 7 is a graph of tensile force in newtons versus elongation at 37° C.

FIG. 7 is a graph of tensile force versus elongation at 37° C. for the test plate of FIG. 6 which excludes a copolymer additive of the present invention and the test plates of FIG. 6 which include copolymer additives of the present invention. The test piece which excludes the copolymer additive shows desirable tensile force at 37° C., however, it remains brittle at room temperature. In contrast, the test plates of the present invention are bendable at both room temperature and 37° C.

Figure 8:
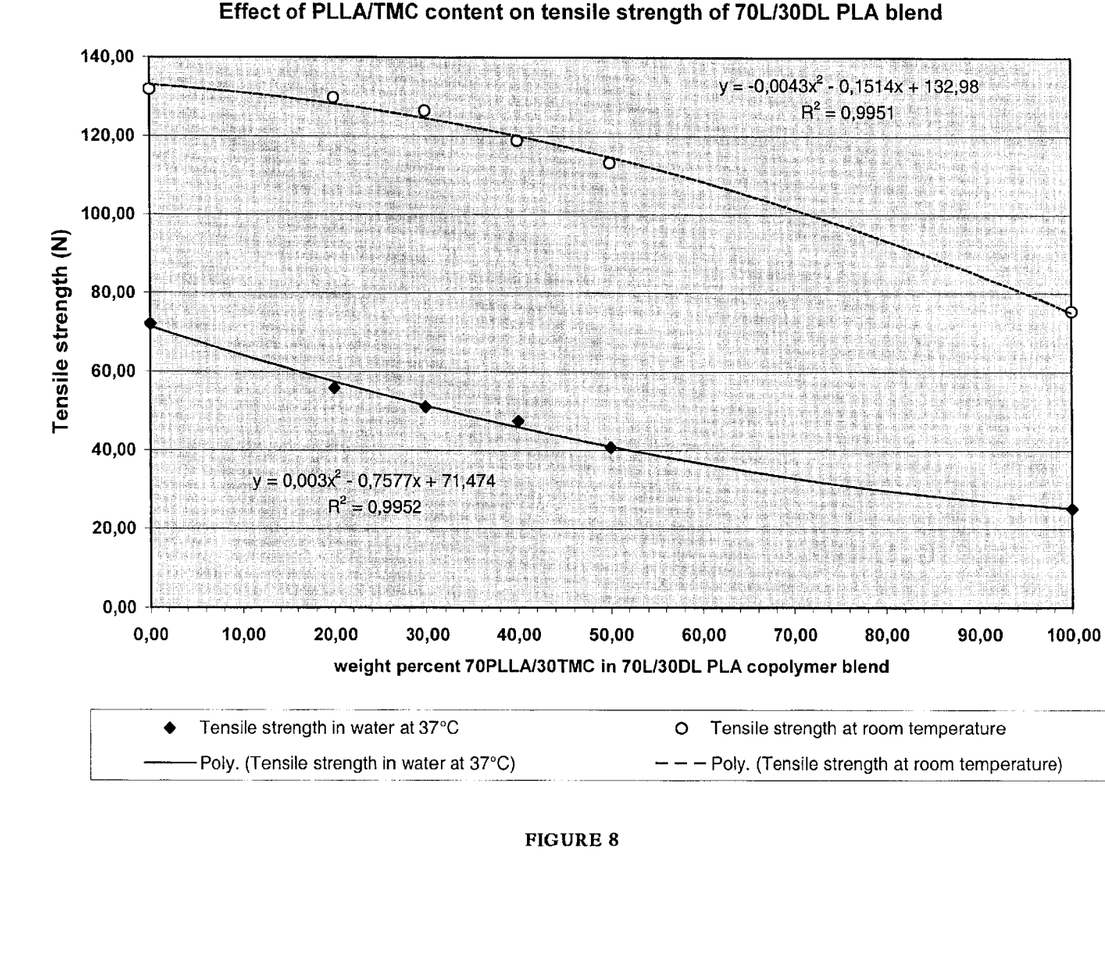
FIG. 8 is a graph of tensile strength in newtons of implants versus weight percent of the copolymer additive of the present invention in the implant at room temperature and at 37° C.

FIG. 8 is a graph of tensile strength versus weight percent of copolymer additive which further demonstrates the brittle nature at room temperature of the test piece which lacks the copolymer additive.

Figure 9:
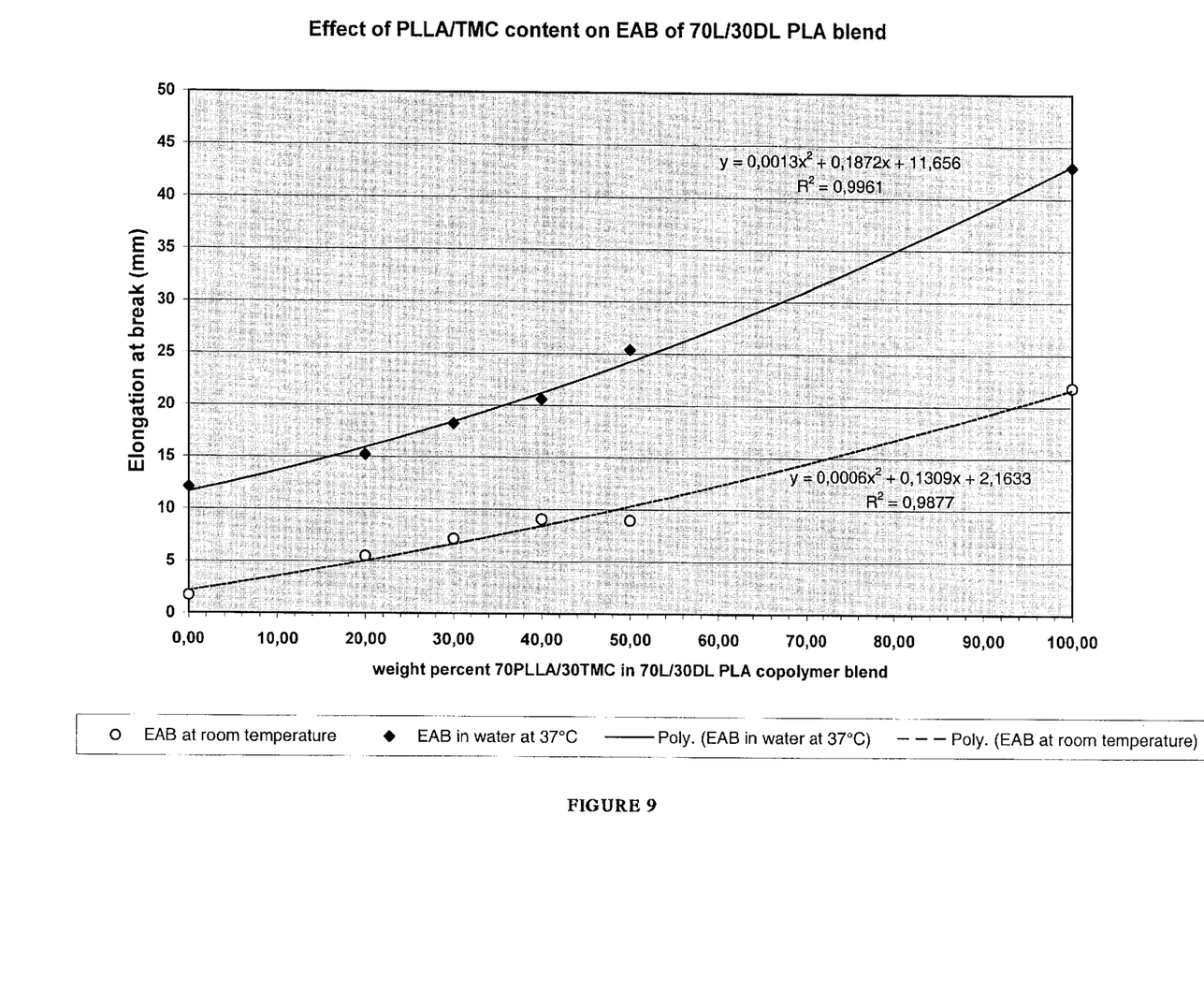
FIG. 9 is a graph of elongation at break in mm of implants versus weight percent of the copolymer additive of the present invention in the implant at room temperature and at 37° C.

FIG. 9 is a graph of elongation at break versus weight percent of copolymer additive which further demonstrates the brittle nature at room temperature of the test piece which lacks the copolymer additive.

Figure 10:
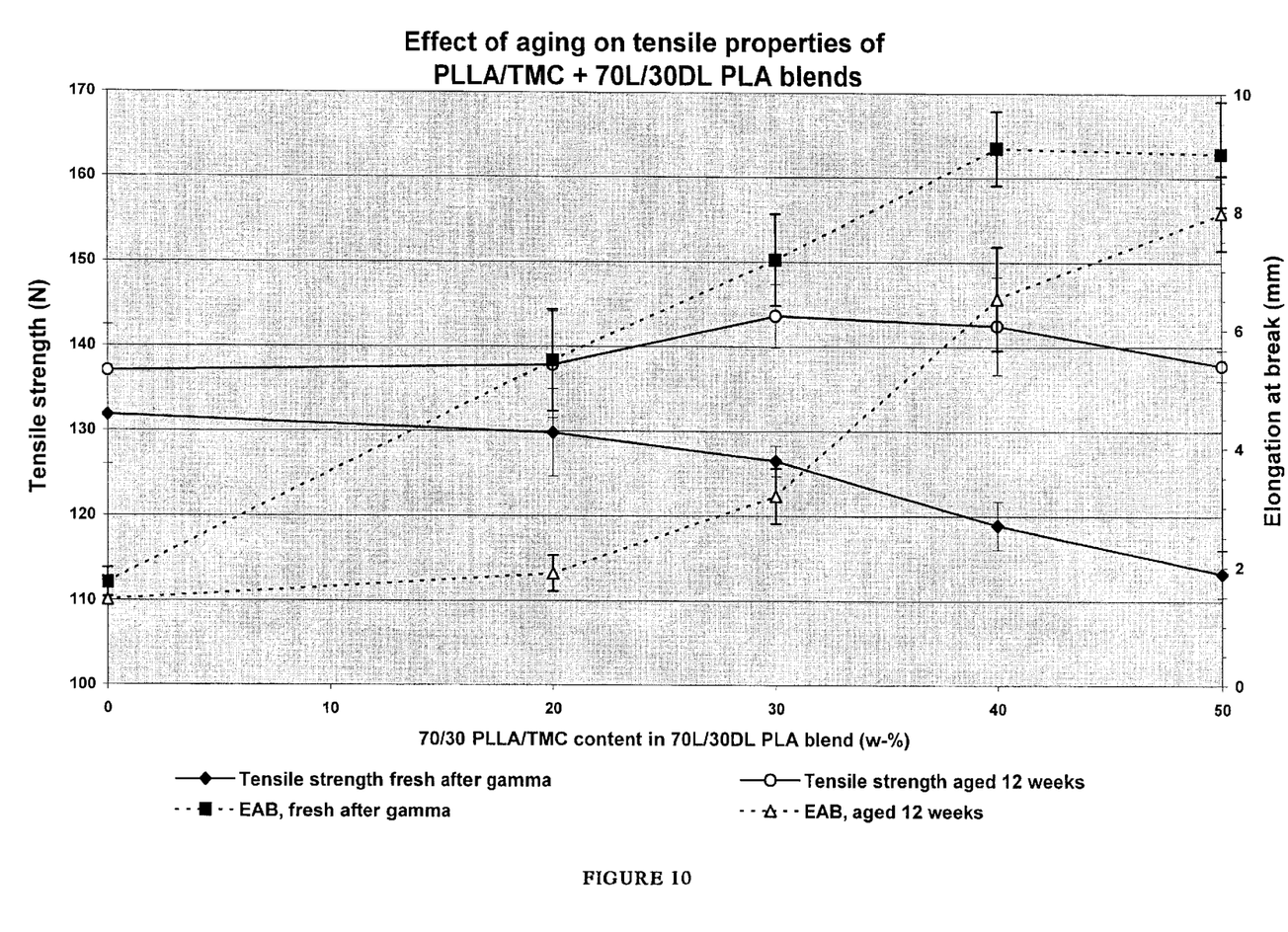
FIG. 10 is a graph of tensile strength and elongation at break of various implants after production and after 12 weeks storage.
Figure 11:
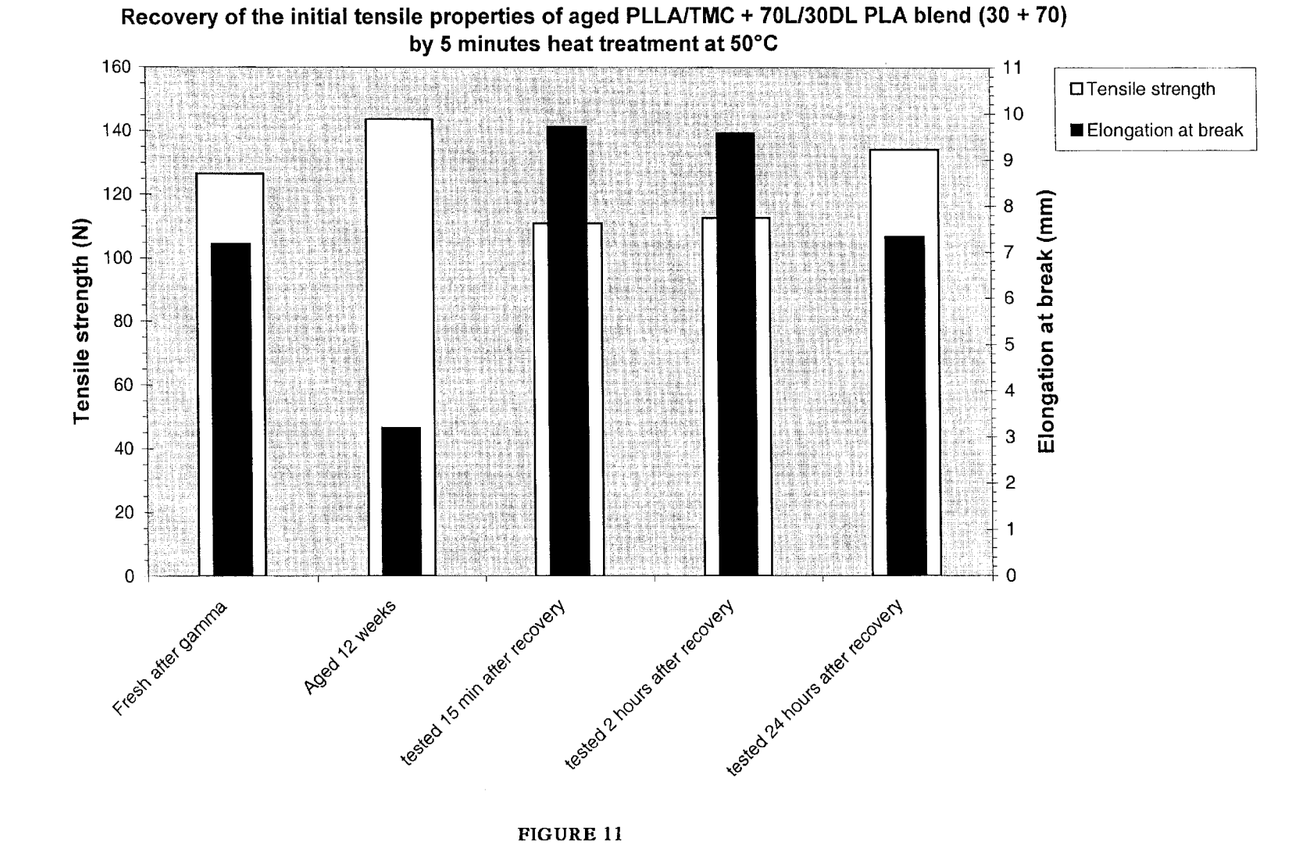
FIG. 11 is a graph showing the recovery of initial tensile properties of various aged implants by 5 minute heat treatment at 50° C.

FIG. 10 is graph of tensile strength and elongation at break of various implants after production and after 12 weeks storage. The elongation at break becomes lower as shelf life increases due the effects of aging. It is believed that the polymer chains reorganize over time to decrease free volume and to increase the glass transition temperature of the test plate and to thereby increase the tensile strength of the test plate, thereby reducing the cold-bending ability of the test plate. However, FIG. 11 is a graph showing the recovery of initial tensile properties of various aged implants by immersing the test plate in water at 50° C. for 5 minutes. When the test plate is heated, the polymer chains return to their original confirmation and the free volume increases to thereby decrease the tensile strength of the test plate. According to this aspect of the invention, therefore, a method of recovering initial physical properties of implants, such as lower tensile strength, formed from the polymer compositions of the present invention is presented wherein, the tensile strength of the implant is allowed to increase, such as for example, at room temperature. The implant is then heated above room temperature for a time period sufficient to lower the tensile strength at room temperature of the implant. According to the present invention, the test piece including the copolymer additive maintains its lowered tensile strength when rejuvenated for a longer period of time, i.e. several hours to several days, as compared to test pieces which do not include the copolymer additive, i.e. a few second to a few minutes.

It is to be understood that the embodiments of the invention, which have been described, are merely illustrative of some applications of the principles of the invention. Numerous modifications may be made by those skilled in the art without departing from the true spirit and scope of the invention.

What is claimed is:

1. A method of making implants comprising
melt-blending a mixture of a base material and a copolymer additive to form a melt-blended mixture,
forming an implant from the melt-blended mixture, wherein the implant has a tensile strength at room temperature that is lower than a tensile strength at room temperature for an implant formed from the base material excluding the copolymer additive.

2. An implant formed from a melt-blended polymer composition comprising:
a base material including a biodegradable polymer or copolymer, and
a copolymer additive including one or more monomers imparting a tensile strength for the implant at room temperature that is lower than a tensile strength at room temperature for an implant formed from the base material excluding the copolymer additive.

3. A method of making implants comprising
melt-blending a mixture of a base material and a copolymer additive to form a melt-blended mixture,
forming an implant from the melt-blended mixture, wherein the implant has a glass transition temperature at room temperature that is lower than a glass transition temperature for an implant formed from the base material excluding the copolymer additive.

4. A method of recovering initial tensile strength of an implant comprising
melt-blending a mixture of a base material and a copolymer additive to form a melt-blended mixture,
forming an implant from the melt-blended mixture,
allowing the tensile strength of the implant to increase, and
heating the implant in a manner to decrease the tensile strength of the implant for a time period greater than a few minutes.

5. A medical implant comprising melt-blended polymer composition comprising:
a base material including a biodegradable polymer or copolymer, and
a copolymer additive including one or more monomers imparting a tensile strength for the melt-blended polymer composition at room temperature that is lower than a tensile strength at room temperature for the base material.

6. The medical implant of claim 5 wherein the base material is a polymer or copolymer including a lactide.

7. The medical implant of claim 5 wherein the base material is selected from the group consisting of polylactides, polyglycolides, poly(L-lactide), poly(D-lactide), poly(L-lactide-co D,L-lactide), poly(L-lactide-comeso-lactide), poly(L-lactide-co-glycolide), poly(L-lactide-co-epsilon-caprolactone), poly(D,L-lactide-co-meso-lactide), poly(D,L-lactide-co-glycolide), poly(D,L-lactide-co-epsilon-caprolactone), poly(meso-lactide-co-glycolide), and poly(meso-lactide-co-epsilon-caprolactone).

8. The medical implant of claim 5 wherein the copolymer additive includes trimethylene carbonate or dioxanone.

9. The medical implant of claim 5 wherein the base material is selected from the group consisting of poly(L-lactide-co-D,L-lactide) 70:30, poly(L-lactide-co-D,L-lactide) 80:20, poly(L-lactide-co-glycolide) 85:15, and poly(L-lactide-co-glycolide) 80:20.

10. The medical implant of claim 5 wherein the copolymer additive is selected from the group consisting of poly(L-lactide-co-trimethylene carbonate), poly(D,L-lactide-co trimethylene carbonate), poly(meso-lactide-co-trimethylene carbonate), poly(glycolide-co-trimethylene carbonate), poly(L-lactide-co-dioxanone), poly(D,L-lactide-co-dioxanone), poly(meso-lactide-co-dioxanone), and poly(glycolide-co-dioxanone).

11. The medical implant of claim 5 wherein the copolymer additive is poly(L-lactide-co-trimethylene carbonate).

12. The medical implant of claim 5 wherein the base material is present in an amount of between about 50% and 99% and the copolymer additive is present in an amount between 1% and 50%.

* * * * *